United States Patent [19]

Drillio

[11] Patent Number: 4,854,308
[45] Date of Patent: Aug. 8, 1989

[54] KNEE ORTHOSIS HAVING OFFSET WITHIN HINGES AND ANTI-ROTATION STRAPS

[76] Inventor: Robert C. Drillio, 41 Whitehall Ln., Reading, Mass. 01867

[21] Appl. No.: 138,805

[22] Filed: Dec. 28, 1987

Related U.S. Application Data

[63] Continuation-in-part of Ser. No. 2,269, Dec. 29, 1986, abandoned.

[51] Int. Cl.[4] ............................................. A61F 5/04
[52] U.S. Cl. .................... 128/80 C; 128/80 F
[58] Field of Search ............... 128/80 C, 80 F, 80 G, 128/88; 2/339

[56] References Cited

U.S. PATENT DOCUMENTS

| | | | |
|---|---|---|---|
| 1,838,688 | 12/1931 | Landresse | 2/339 |
| 2,270,881 | 1/1942 | Lang | 2/339 |
| 2,587,490 | 2/1952 | Krieger | 2/339 |
| 2,883,982 | 4/1959 | Rainey | 128/80 F |
| 3,055,359 | 9/1962 | Palmer | 128/88 |
| 3,350,719 | 11/1967 | McClure | 2/22 |
| 3,581,741 | 6/1971 | Rosman | 128/80 C |
| 3,669,105 | 6/1972 | Castiglia | 128/80 |
| 3,817,244 | 6/1974 | Taylor | 128/80 |
| 3,844,279 | 10/1974 | Konvalin | 128/80 |
| 3,898,697 | 8/1975 | Whitehead | 2/22 |
| 3,902,482 | 9/1975 | Taylor | 128/80 F |
| 3,945,047 | 3/1976 | Jarrell | 2/24 |
| 3,958,569 | 5/1976 | Vosburgh | 128/80 |
| 4,088,130 | 5/1978 | Applegate | 128/80 |
| 4,271,831 | 6/1981 | Deibert | 128/80 |
| 4,320,747 | 3/1982 | Daniell | 128/80 |
| 4,361,142 | 11/1982 | Lewis et al. | 128/80 |
| 4,381,768 | 5/1983 | Erchsen et al. | 128/80 C |
| 4,463,751 | 8/1984 | Bledsoe | 128/80 |
| 4,503,846 | 3/1985 | Martin | 128/80 C |
| 4,506,661 | 3/1985 | Foster | 128/80 C |
| 4,520,802 | 6/1985 | Mercer et al. | 128/80 |
| 4,556,053 | 12/1985 | Irons | 128/80 C |
| 4,565,190 | 1/1986 | Pirmantgen et al. | 128/80 |
| 4,624,247 | 11/1986 | Ford | 128/80 C |
| 4,633,867 | 1/1987 | Kausek et al. | 128/80 C |

FOREIGN PATENT DOCUMENTS 2724586 12/1978 Fed. Rep. of Germany.

OTHER PUBLICATIONS

Harry W. Woodward, A Knee Brace, Date Unknown, Colorado Springs, Colorado, pp. 1024–1025.

Primary Examiner—Edgar S. Burr
Assistant Examiner—Tonya Lamb
Attorney, Agent, or Firm—Hamilton, Brook, Smith & Reynolds

[57] ABSTRACT

The application is directed to a knee orthosis having a proximal cuff, (2), engageable with the wearer's leg above the knee, a distal cuff, (4), engageable with the wearer's leg below the knee, and a pair of polycentric hinges, (6), joining the cuffs. Both of the hinges are offset in a medial direction relative to the wearer's leg to prevent pressure on the fibula head. Stop means, (110 and 112), limit the pivotal motion of both the hinges relative to the cuffs to approximately 180° measured in the anterior direction to prevent the wearer's knee from canting rearwardly.

32 Claims, 10 Drawing Sheets

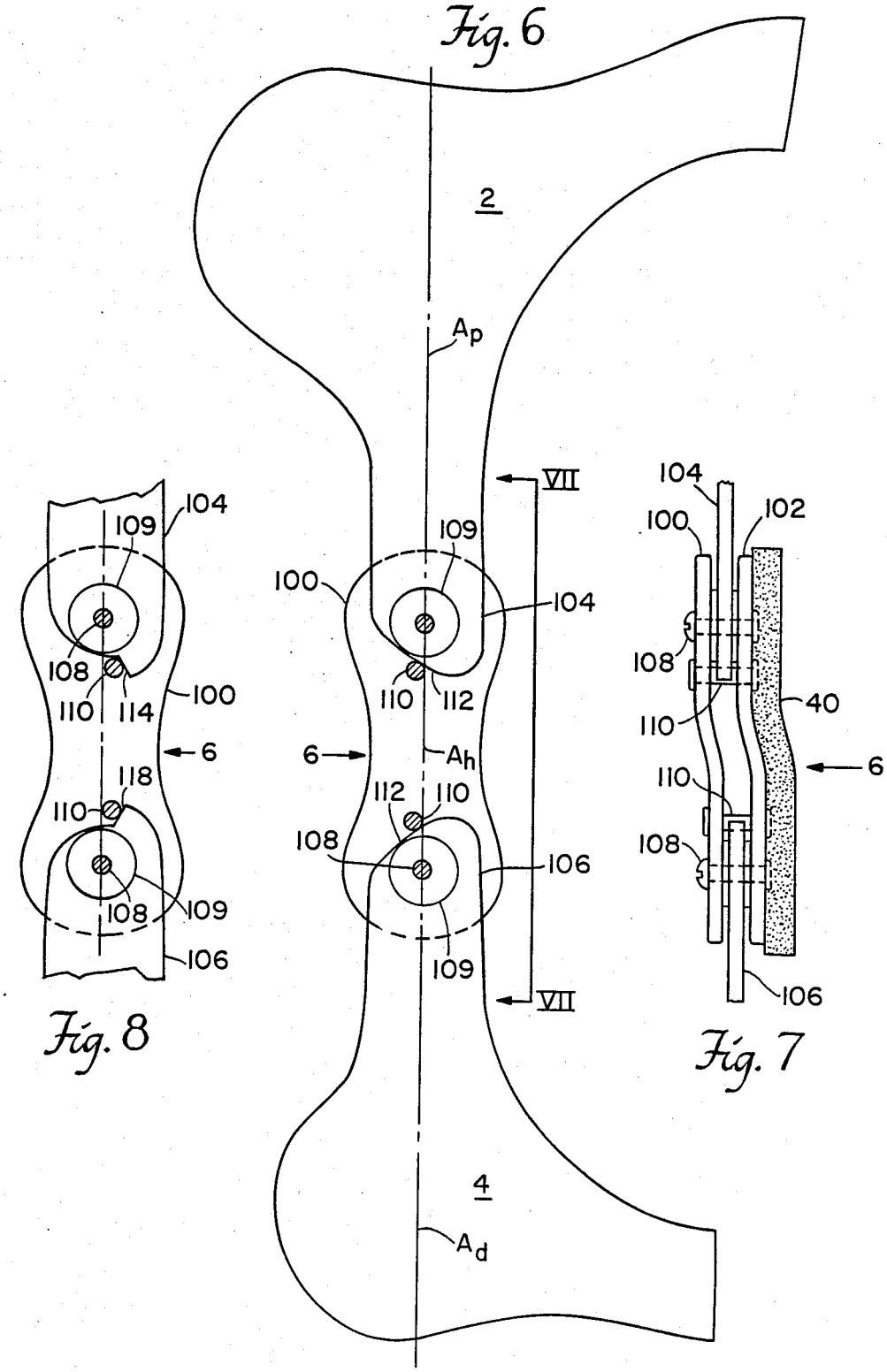

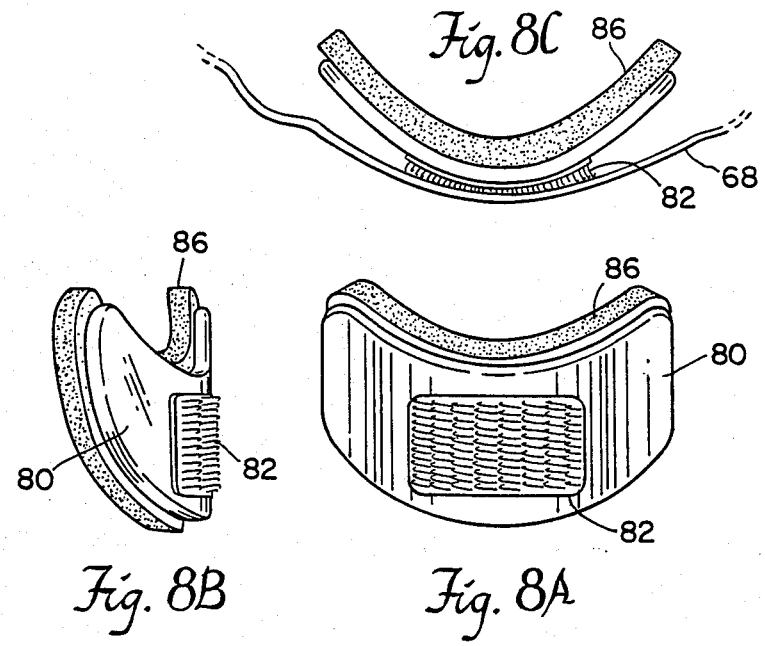
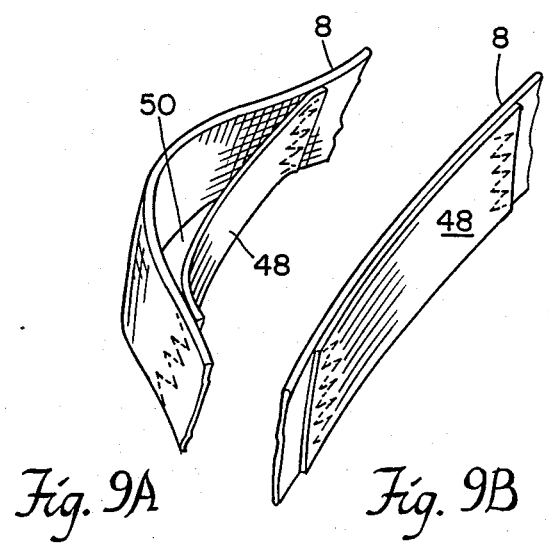

KNEE ORTHOSIS HAVING OFFSET WITHIN HINGES AND ANTI-ROTATION STRAPS

RELATED CASE

This Application is a Continuation-in-Part of my corresponding Application, Ser. No. 002,269, filed 12-29-86; now abandoned.

FIELD OF THE INVENTION

This invention relates to a knee orthosis and particularly to one which is lightweight, comfortable, adjustable to the individual wearer, and which has particular value for athletes participating in sports.

BACKGROUND OF THE INVENTION

Orthotic devices have been in use for a many years, perhaps, dating back for centuries. While they afford varying degrees of support or protection for portions of the human body, they all possess a common shortcoming of rendering the body less mobile than when no device is worn.

It is obvious that a "perfect" orthotic device would render the wearer as mobile as if he were not wearing a device and yet afford support or protection against injury or further injury to a weakened joint, permitting the wearer to continue in a physical activity in which he could not participate without the device.

Athletes, particularly contact sports players, are quite prone to knee injuries, which if sufficiently severe could leave a person immobile, or to a lesser degree, not as effective in running, jumping, or the like. Continued participation by an injured athlete leaves him prone to further injury to the already damaged member.

It is one of the objectives of this invention to provide a knee orthosis or knee brace, which is designed to reduce the possibility of injury due to a lateral or anterior impact, while permitting the athlete as much freedom as is possible. Inherent in this objective is that the knee orthosis or brace should concurrently be as strong as possible, as comfortable as possible, and as light as possible.

It is also an objective of this invention to produce a knee orthosis which may be formed or custom fit to the individual wearer, and which, after being fit to the wearer, is adjustable relative to how much pressure it puts on the leg of the wearer, and how much support it offers to a specifically injured area such as the patella tendon.

SUMMARY OF THE INVENTION

The invention resides in a knee orthosis which is made of lightweight, high impact plastic to afford protection against impact and which may be formed to the shape of the individual wearer's leg. The plastic is padded with thick, durable, non-allergenic foam. The orthosis, or brace, includes a proximal cuff, which is engageable with a wearer's leg above the knee. A distal cuff is engageable with the wearer's leg below the knee. The cuffs are joined by a pair of polycentric hinges, each of which has a proximal portion pivotally attached to the proximal cuff, and a distal portion spaced from the proximal portion and pivotally attached to the distal cuff. The proximal portion of both hinges is offset relative to the distal portion in the medial direction relative to the wearer's leg to prevent pressure to the fibula head and to contour as close to the leg configuration as possible.

The hinges comprise two substantially figure eight shaped members pivotally secured on opposite sides of the proximal and distal cuffs.

The proximal and distal portions of each hinge have stop means to limit the pivotal motion of the proximal and distal portions of the hinges relative to the cuffs to approximately 180° measured in the anterior direction to prevent the wearer's knee from canting rearwardly. The stop means comprise a pair of pins fixed in the hinges which are engaged by stop surfaces formed on the proximal and distal cuffs.

The cuffs do not completely encircle the leg, but rather, each has an arcuate portion which engages the anterior portion of the wearer's leg, the proximal cuff engaging above and the distal cuff engaging below the knee. Each cuff includes an extending portion which is pivotally attached to one of the polycentric hinges. The cuffs and the hinges together with their padded inner surfaces offer resistance to impact.

A pair of non-elastic, removable, adjustable straps are secured, one each, to the proximal and distal cuffs for engagement with the wearer's posterior thigh and calf respectively. The non-elastic straps each include an elasticized bridging insert on their inner surface, which bridging, directly engages the skin and permits muscle expansion and contraction at the quadricep and calf.

In addition, there also are a pair of non-elastic straps secured, one each, to the lateral portions of the proximal and distal cuffs. These non-elastic straps engage the posterior of the leg and are so positioned to leave the popliteal space open for ease of flexation.

A pair of adjustable, elasticized straps are secured, one each, to the proximal and distal cuffs adjacent the proximal and distal portions of the polycentric hinges for engagement with the anterior of the wearer's leg above and below the knee. The distal elasticized strap may have a removeable, non-allergenic foam pad secured to its inner surface for engagement directly with the wearer's leg above the patella tendon.

Once the plastic cuffs have been formed to fit the particular contours of the wearer's leg, the knee orthosis must be worn with the foam padding on the skin. It may be tightened or loosened for comfort, and to afford the degree of pressure on the leg that the wearer desires.

The padded polycentric hinges, which are esentially shaped in a figure eight configuration, afford protection particularly to a lateral impact, and the fact that the hinges employ stop means to limit the pivotal motion of the hinges relative to the cuffs to 180° measured in the anterior direction prevents the wearer's knee from canting rearwardly as it otherwise would with an anterior or frontal impact.

The knee is not prevented from bending or yielding to a posterior or rearward impact since this is the direction that the knee would normally yield.

The above and other features of the invention, including various novel details of construction and combinations of parts, will now be more particularly described with reference to the accompanying drawings and pointed out in the claims. It will be understood that the particular knee orthosis embodying the invention is shown by way of illustration only and not as a limitation of the invention. The principles and features of this invention may be employed in varied and numerous embodiments without departing from the scope of the invention.

DESCRIPTION OF THE DRAWINGS

FIG. 6 is a schematic medial view of a portion of the proximal and distal cuffs and one polycentric hinge joining them.

FIG. 7 is a sectional view of a polycentric hinge taken on the lines VII—VII on FIG. 6.

FIG. 8 is a distal view of an alternative configuration of the polycentric hinge shown in FIG. 7.

FIGS. 8A, 8B, and 8C are detail views of a pad employed with the orthosis.

FIGS. 9A and 9B are detail views of an elasticized, bridging member employed with the orthosis.

DETAILED DESCRIPTION OF THE INVENTION

Figure 1:
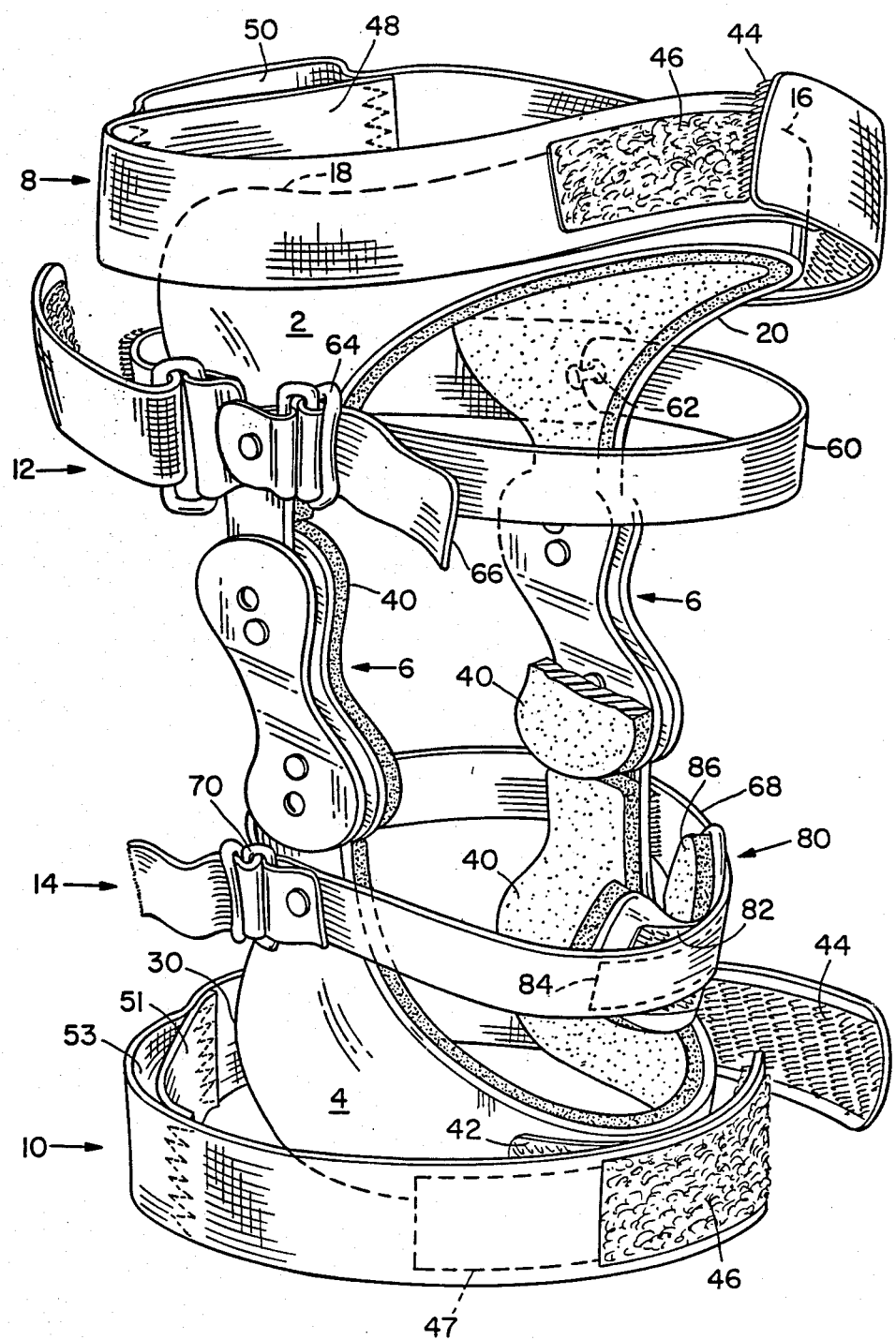
FIG. 1 is a perspective view of a knee orthosis, embodying the features of present invention for a wearer's left leg.

As will be seen in FIGS. 1, 2, 3, the knee brace, or knee orthosis embodying the invention, comprises three basic parts: an upper or proximal cuff, 2, which is engageable with a wearer's leg above the knee, a distal cuff, 4, which is engageable with the wearer's leg below the knee, and a pair of polycentric hinges, 6, which pivotally join the cuffs together. Straps and their associated attaching hardwear are indicated generally by the reference characters 8, 10, 12, and 14, and secure the brace to the wearer's leg.

Figure 4:
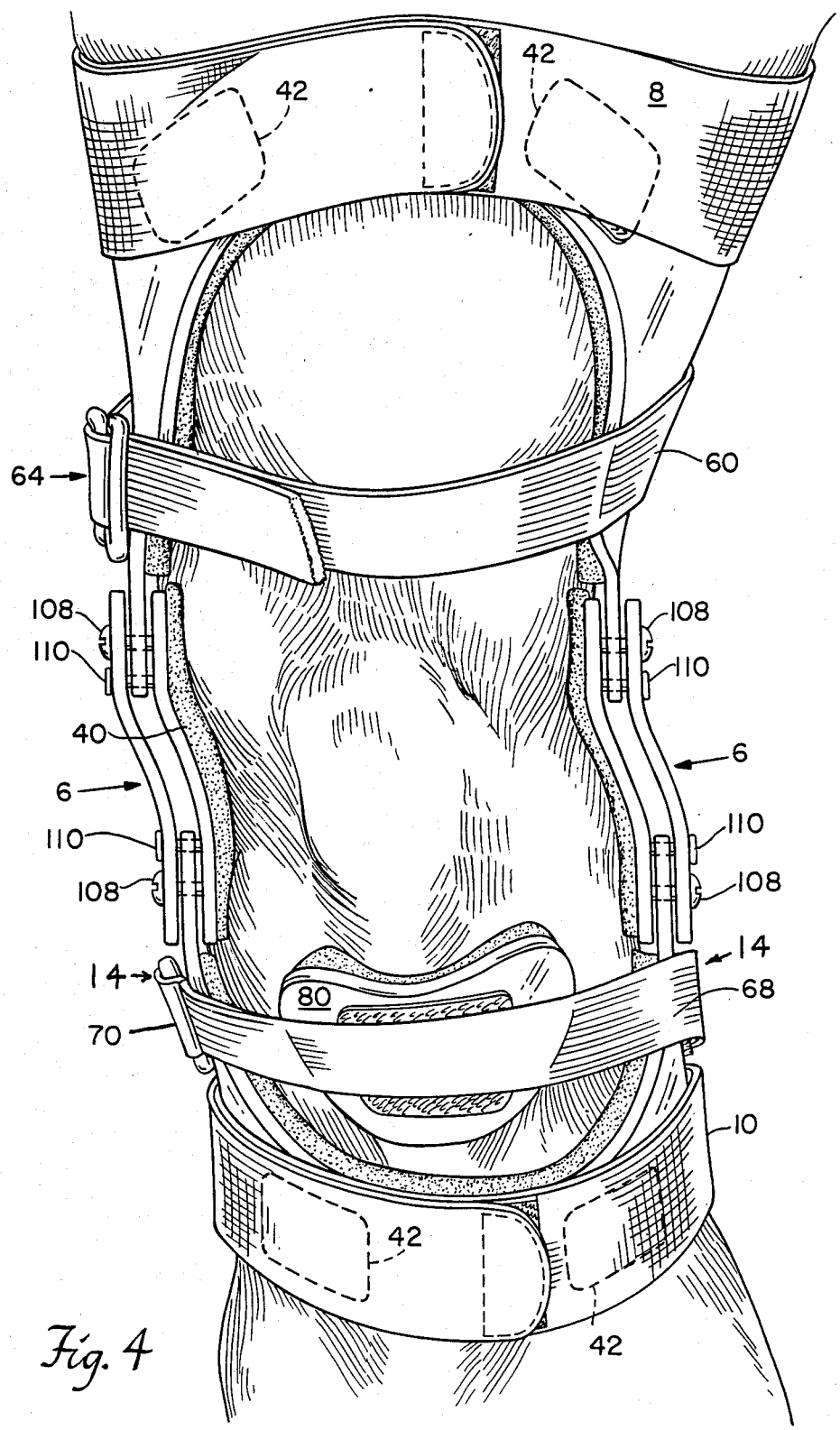
FIG. 4 is a front or anterior view of the orthosis on a wearer's left leg.
Figure 5:
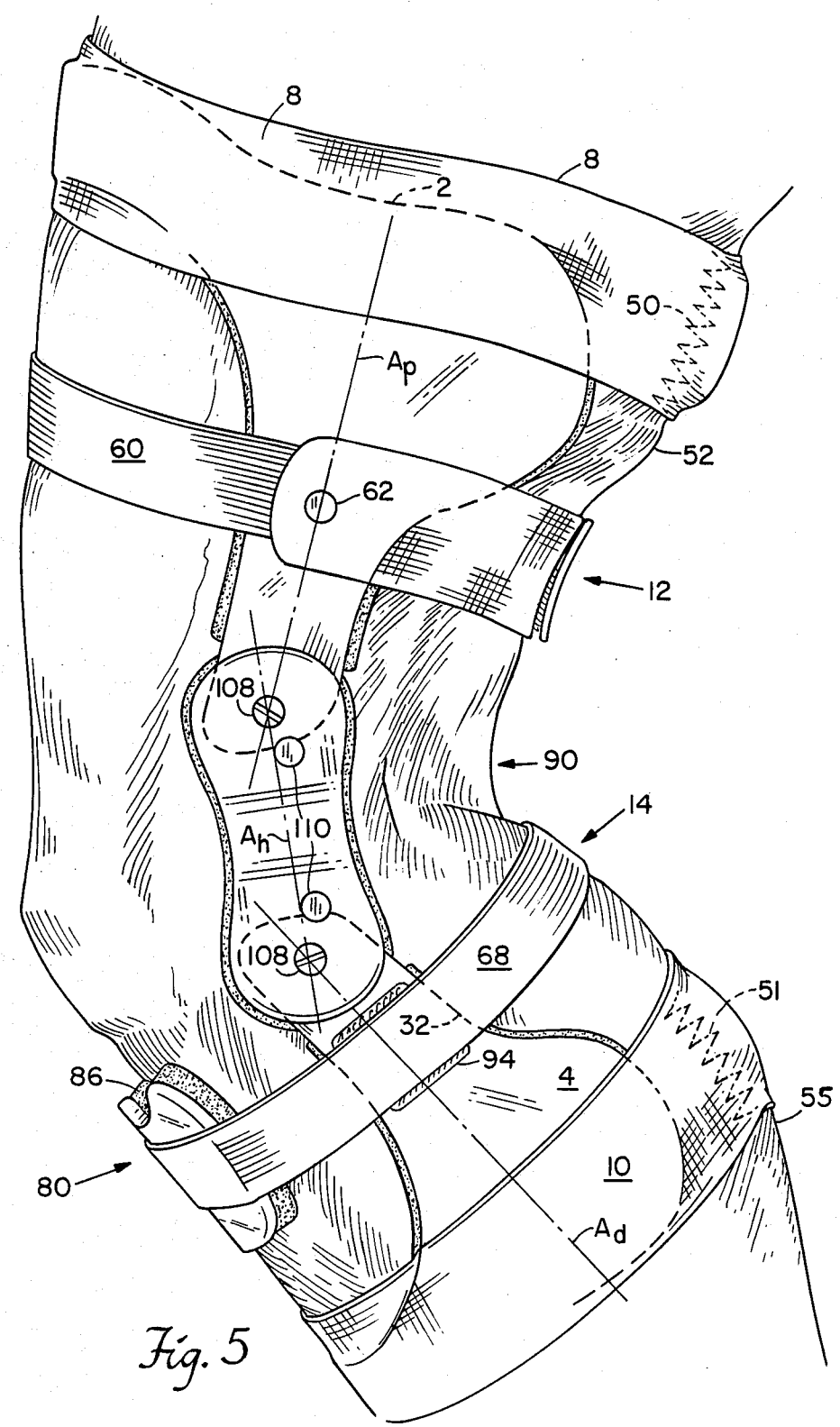
FIG. 5 is an outside view of the orthosis on a wearer's left leg.

The brace shown in the drawings is constructed to fit a left leg as will become apparent hereinafter. FIGS. 4 & 5 show the brace attached to a leg.

The upper or proximal cuff, 2, is formed to fit the anterior portion of the wearer's legs, and is esentially curvilinelar in configuration. It includes a front arcuate portion, 16, and two curved lateral portions, 18 and 20. The cuff is open at the posterior portion so that it may be placed over the knee from the anterior or front. The cuff has lateral depending portions, 22 and 24. The distal cuff, 4, is similarly constructed and includes an arcuate portion, 28, curved side portions, 30 and 32, and lateral portions, 36 and 38.

Both cuffs, 2 and 4, and the polycentric hinges, 6, are made of lightweight, high impact thermoplastic material which can be formed to fit the contours of the individual wearer's leg. A material found satisfactory for this purpose is sold under the tradename LEXAN by the General Electric Company.

Both cuffs, 2 and 4, and the hinges, 6, are padded on the inside by a durable non-allergenic foam pad, 40. The padded cuffs and hinges are positioned to absorb anterior or frontal impacts, as well as lateral impacts to the outside of the leg and medial impacts to the inside of the leg.

The cuffs are secured to the leg by a plurality of straps one of which is a non-elastic web strap, 8. It is releasably secured to the proximal cuff, 2, by any suitable means such as, hook cloth to engage pads of pile cloth, 42, on the cuff. The strap extends around the posterior portion of the thigh and is adjustably joined at the anterior or front of the cuff, 2, by hook and pile cloth best seen in FIG. 1, and comprising hook cloth, 44, and pile cloth, 46, secured to the outer and inner surfaces of the strap, 8, respectively.

Whereas the strap, 8, is non-elastic, but adjustable in length by the hook and pile cloth, an elastic bridge, 48, (FIG. 1), is sewn to the inner surface of the strap leaving a gap, 50, at the rear of the strap. When applied to a leg as shown in FIG. 5, the elastic bridge permits muscle expansions in the quadricep, 52.

The strap, 10, is similar to the strap, 8, and is secured to the distal cuff, 4, by hook and pile material including hook material, 44, and pile material, 46. The strap is attached to the cuff with pile material, 47, including pads of hook material, 44, secured to the cuff. Strap 10 also includes a bridge of elastic material, 51, which in unstretched condition creates a gap, 53, in the non-elastic strap, 10. When applied to the leg, the strap, 10, surrounds the calf, as shown in FIG. 5, permitting contraction and expansion of the calf muscle, 55.

Details of the bridges, 48 and 51, are seen in FIGS. 9a and 9b.

Again referring to FIG. 1, an elastic strap portion, 60, which is part of strap 12 is secured to the proximal cuff, 2, by securing means, such as, a rivet, 62. It is joined to the opposite lateral side of the cuff, 2, by a releasable latching means, 64. The free end, 66, of the elasticized strap is passed through the latching means and pulled to apply the desired amount of tension to the leg at the frontal portion above the knee. A similar elasticized strap, 68 which is part of strap 14, is secured to the distal cuff, 4, and is joined to the opposite side of the distal cuff, 4, by latching means, 70. When applied to the leg, the elasticized strap, 68, is engageable with the leg below the knee on the patella tendon (not shown).

If desired, the strap, 68, may be provided with a non-allergenic foam pad, 80, secured by hook and pile material, 82, 84, respectively to the strap. A foam pad, 86, is secured to the inner surface of the pad, 80, and is directly engageable with the leg below the knee and on the patella tendon as shown in FIG. 5. Details of the pad are shown in FIGS. 8a, 8b, and 8c.

As seen in FIG. 5, the trap portion 60, which is part of strap 12 and 68 which is part of strap 14, engage the posterior of the leg which leaves the popliteal space, 90, open for ease of flexion.

Whereas the entire strap portion, 60, is elasticized and, therefore, flexible, the strap, 68, if desired, may have its flexibility reduced by securing pile cloth, 92 (FIG. 2), to its inner surface, which may be engageable with a pad, 94, of hook cloth secured to the lateral portion, 32, of the distal cuff, 4.

The polycentric hinges, 6, will now be described.

The hinges serve three purposes: a. to permit the proximal and distal cuffs, 2 and 4, to pivot relative to each other and each relative to the hinge itself. b. to serve as protective members against impacts in both the lateral (outside) and medial (inside) directions of the wearer's leg, and, c. to limit the pivotal motion of both proximal and distal portions of the hinges relative to the proximal and distal cuffs, 2 and 4, to approximately 180° measured in the anterior (frontal) direction to prevent the wearer's knee from canting rearwardly.

Referring next to FIG. 6, the hinges, 6, will be seen as including a pair of substantially figure eight shaped members, 100, 102, which lie on both sides of the proximal and distal portions, 104 and 106, of the lateral portions of the cuffs, 2 and 4, respectively. They are secured by a plurality of pivot pins, 108, and washers, 109. The hinges, 6, are lined with a pad of non-allergenic foam material, 40, to protect the knee, particularly the fibula head.

Stop pins, 110, are located parallel with the axis $A_h$ of the hinges as defined by the pins, 108.

The pins, 110, are engageable with stop surfaces, 112, on the portions, 104 and 106, of the proximal and distal cuffs.

As seen in FIG. 8, another embodiment of the stop mechanism will be seen to include angular stop surfaces 114 and 118, on the portions, 104 and 106, of the cuffs.

As viewed in FIG. 5, with the knee flexed, the axes $A_p$ and $A_d$ of the proximal and distal cuffs, are shown at an acute angle relative to each other. This angle will obviously decreases the more the knee flexes, however, it will never exceed 180° maximum which otherwise would permit the knee to cant rearwardly.

Figure 2:
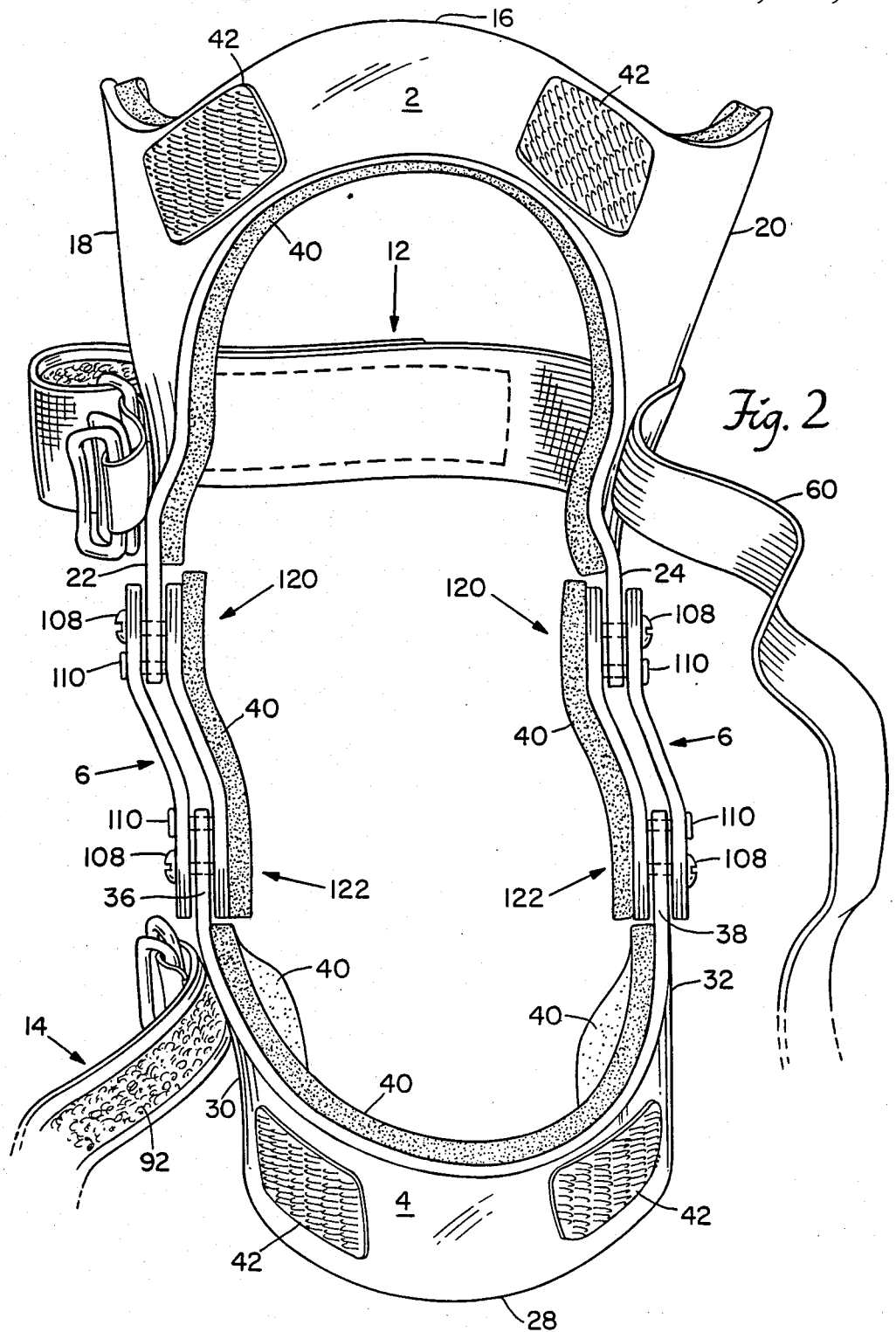
FIG. 2 is a front or anterior view of the orthosis.
Figure 3:
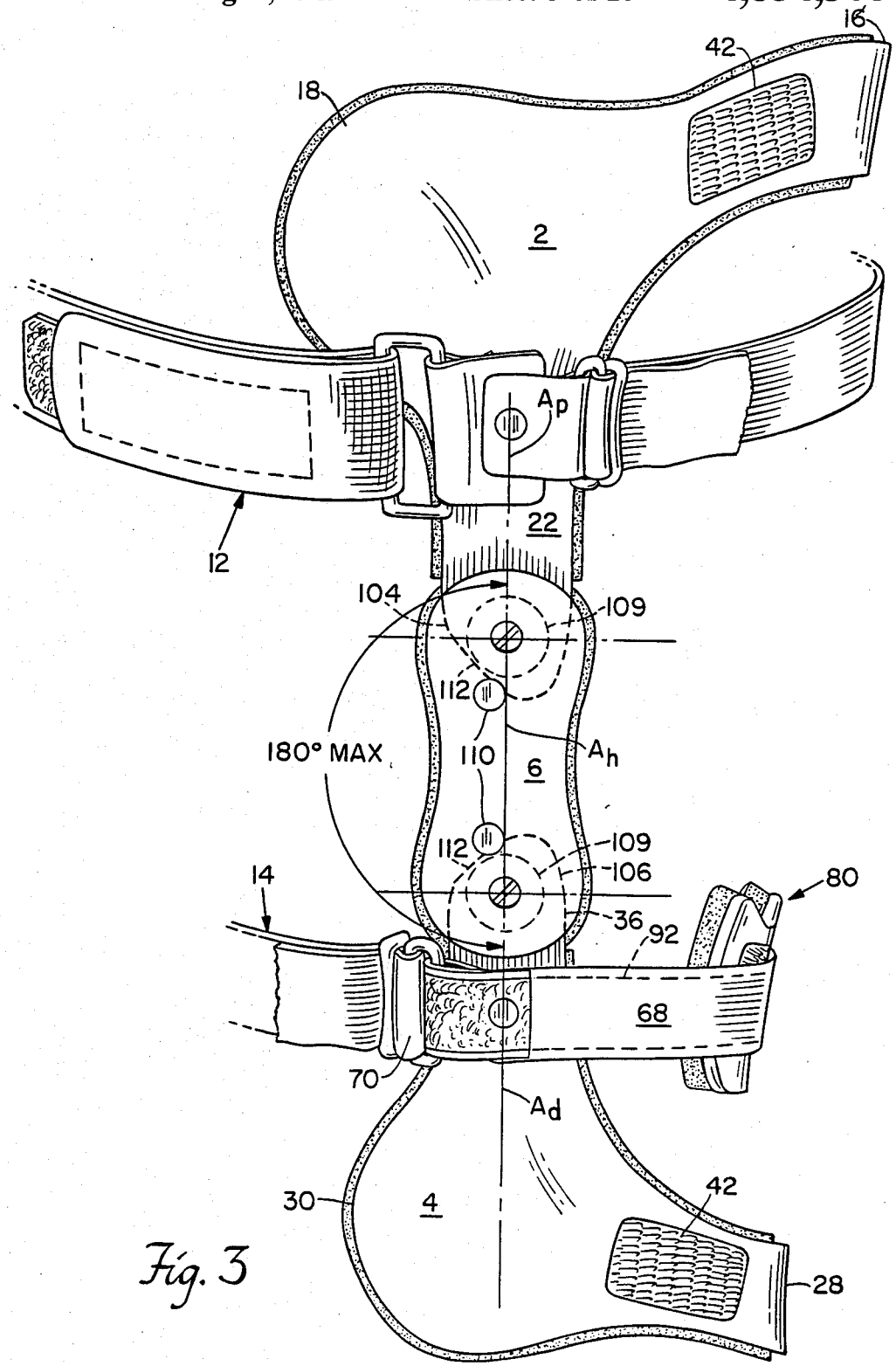
FIG. 3 is an inside, or medial view of the orthosis.

Next referring to FIGS. 2 and 7, it will be seen that the proximal portions, 120, of both hinges, 6, are offset relative to the distal portion, 122 to prevent pressure to the fibula head, 120. Whereas some orthotic devices employ one hinge, which is offset, Applicant has found it to be extremely beneficial and a feature of this invention that both hinges be offset.

Figure 10:
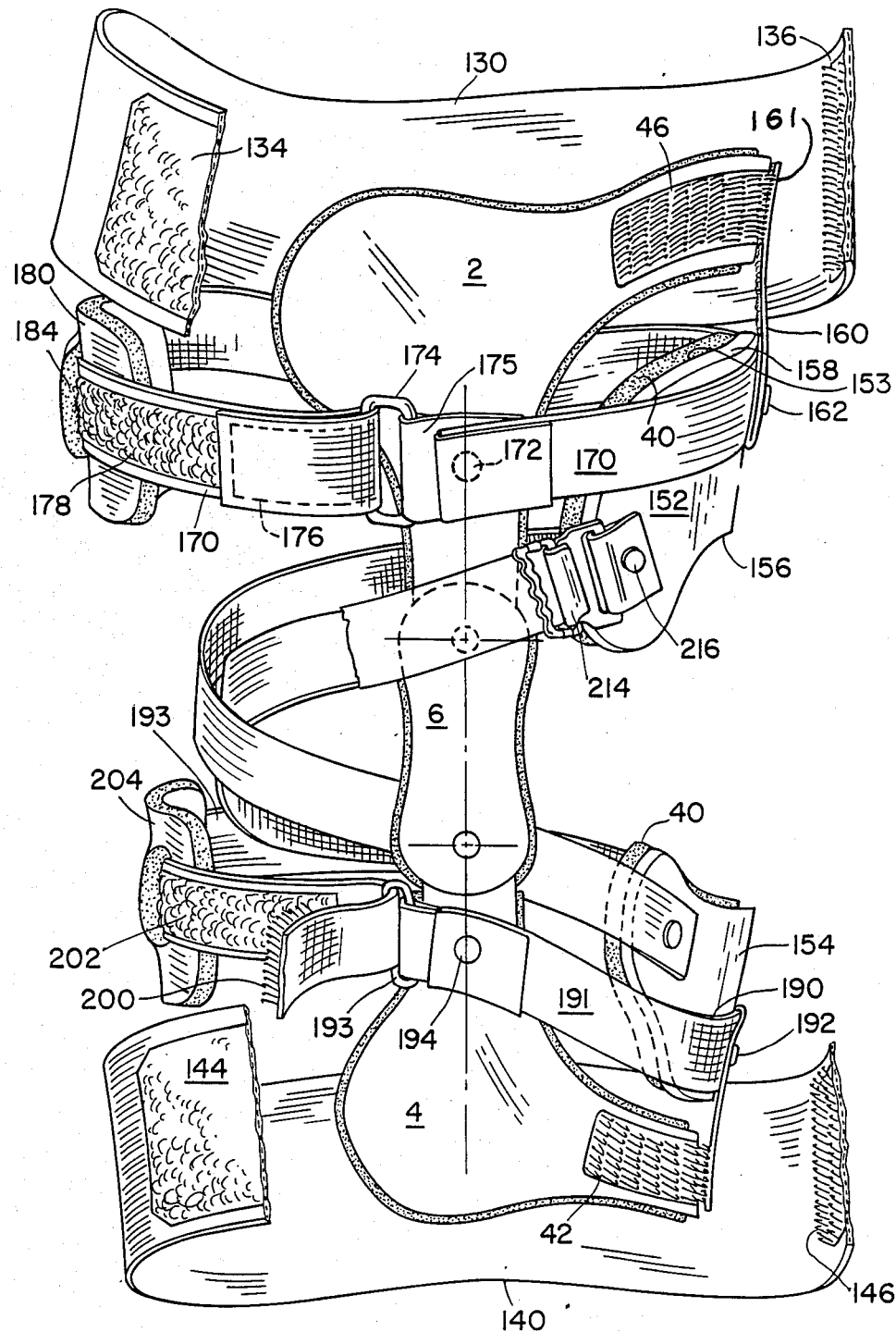
FIG. 10 is an inside, or medial view of another embodiment of my knee orthosis.
Figure 11:
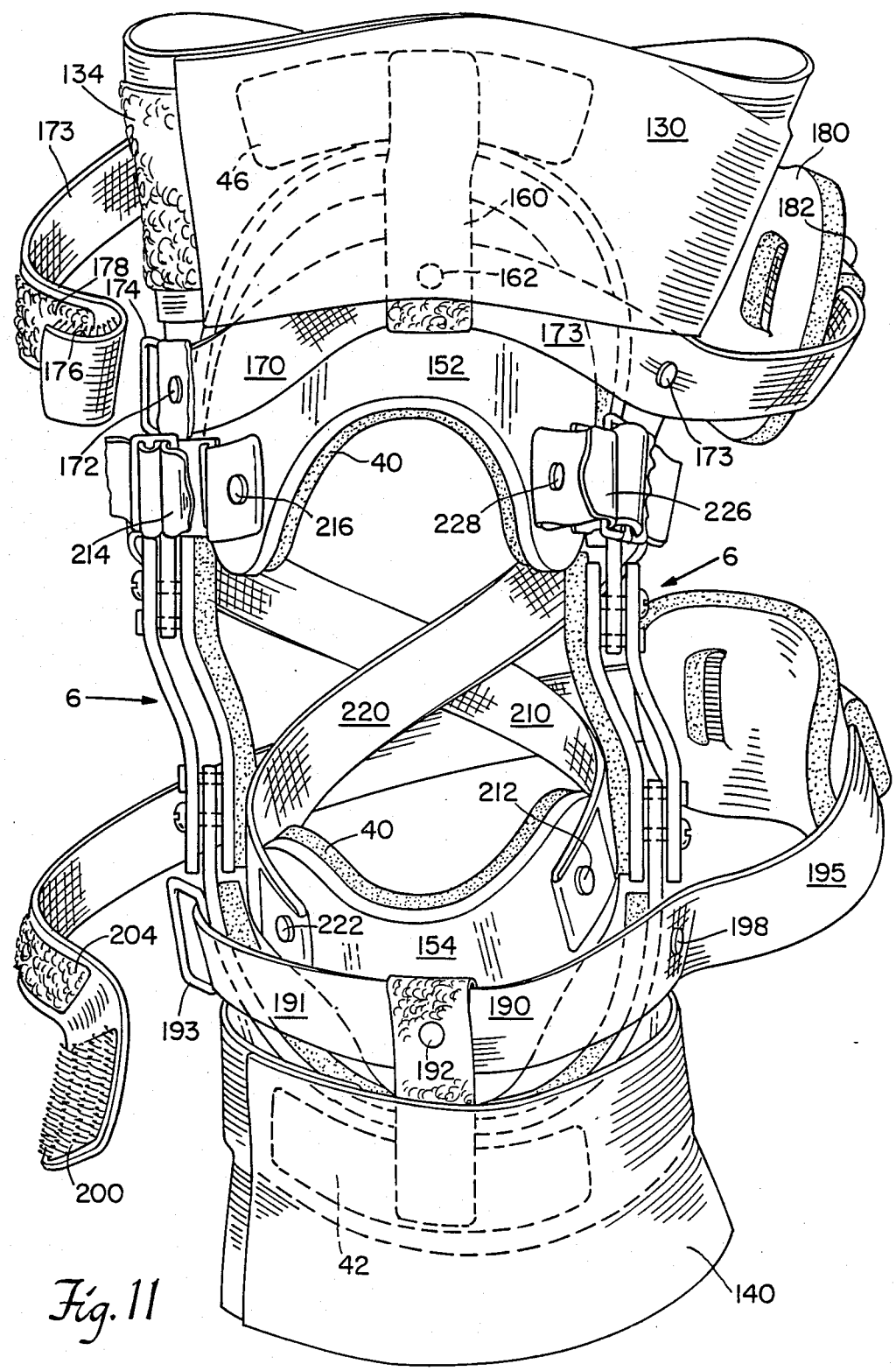
FIG. 11 is a front view thereof.
Figure 12:
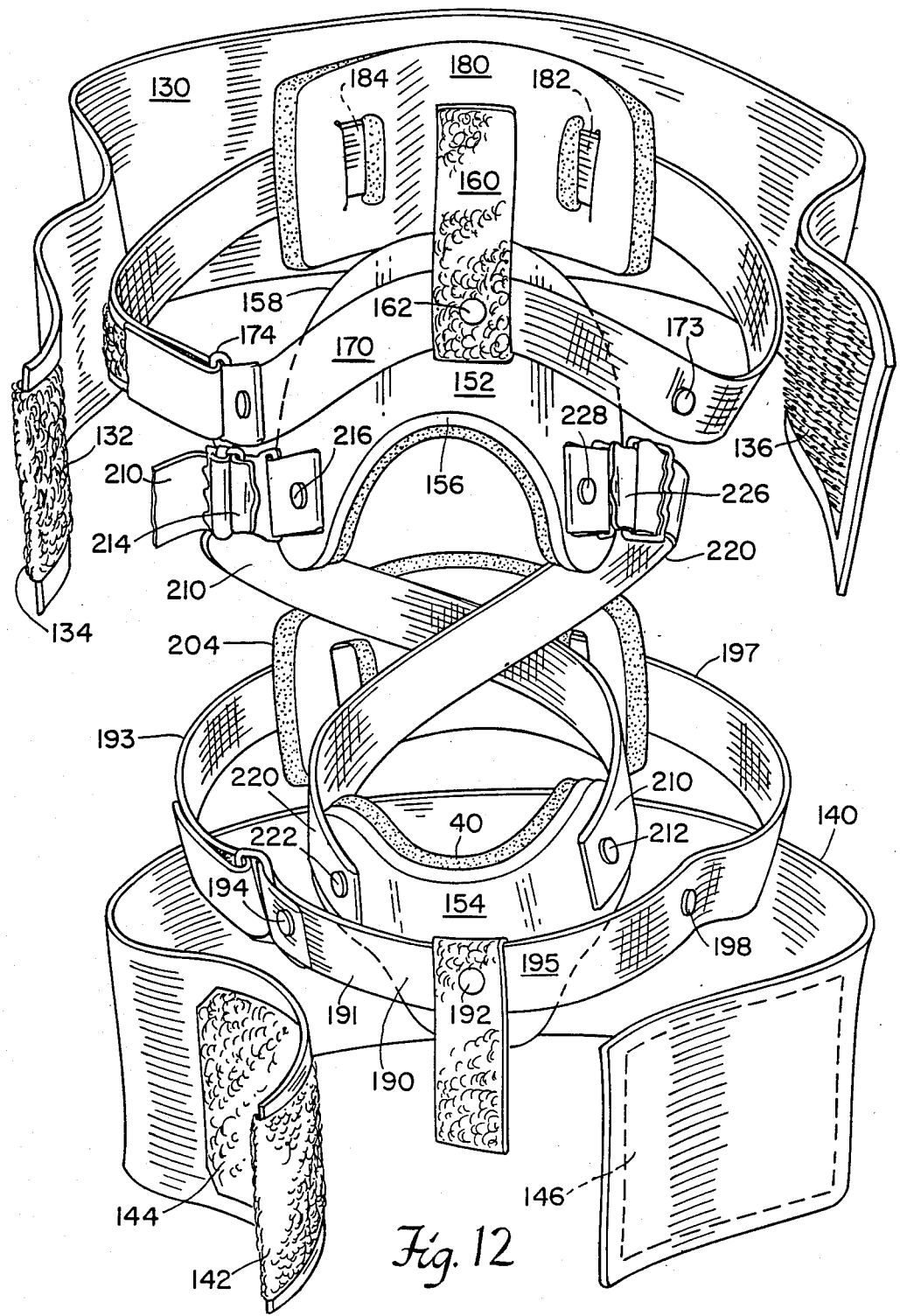
FIG. 12 is a front view of the orthosis of FIG. 10 with the proximal and distal cuffs removed.

A second embodiment of the invention is shown in FIGS. 10 to 12. As in the first environment, there is a proximal cuff 2, a distal cuff 4 and polycentric layers joing them. An upper strap 130 is secured to the front or anterior of the proximal cuff 2. It comprises a relatively wide elasticized band which is removably attached to the proximal cuff 2 by pile cloth 132 (FIG. 12) on the inner surface of the band which engages the hook cloth 46 which is on the frontal portion of the proximal cuff 2. The pile cloth 132 covers the edge and continues around to the outside of the strap as seen at 134 in FIG. 10. With the pile cloth 132 attached to the hook cloth 46, the band 130 is tensioned around the posterior of the leg above the knee. Hook cloth 136 on the inside of the strap overlaps and engages the pile cloth 134. The strap 130 is completely removable.

A similar wide elasticized strap 140 surrounds the leg below the knee and is removably secured to the distal cuff 4 by the pile cloth 142 (FIG. 12) which engages the hook cloth 42 (FIGS. 10 & 11) on the frontal portion of the proximal cuff 4. As is the upper band 130, the lower band or strap 140 is tensioned around the leg. It is joined at the front of the distal cuff by securing a margin 146 of hook cloth to the outside portion 144 of the pile cloth.

The straps 130 and 140 being wider than the strap means 8 and 10 of the first embodiment, and being elasticized, they are better able to apply pressure and support directly to the leg, as well as, functioning to hold the proximal and distal cuffs 2 and 4 in position.

The upper strip 130 offers direct pressure to the super patella tendon above the knee which is the large tendon from the femur to the patella. The function of the strap, in addition to holding the proximal cuff 2 in place, is to stop twisting of the knee. The lower band or strap 140 is positioned on the distal of the patella tendon and is a pressure source. The upper strap 130 applies pressure to the tendon of the quadriceps' extension or the proximal patella tendon and the lower band applies pressure to the distal patella tendon.

Next will be described a plurality of straps and pads forming an antirotation structure. Upper and lower padded pressure applying members 152 and 154 are also known as the super patella plate and the tibia plate respectively, and are designed to engage the frontal portion of the leg directly above and directly below the patella. The upper member and lower members are made of lightweight, thermoplastic, i.e., the same material that the cuffs 2 and 4 and the hinges 6 are made of. The pad 152 has a compound, arcuate, concave interior 153 which is covered with a piece of foam 40 as are the proximal and distal cuffs 2 and 4. It has a lower concave surface 156 and upper convex surface 158. A piece of pile cloth 160 is rivetted at 162 to the pad 152. The upper end 161 of the pile cloth is secured to the hook cloth 46 on the proximal cuff 2.

An elasticized strap 170 is also secured by the rivet 162 to the pad 152. One end of the strap 170 is secured by a rivet 172 to one side of the proximal cuff and the other end by a rivet 173 to the opposite side of the proximal cuff.

A metalic ring 174 is also secured by the rivet 172 and a tab 175 to the proximal cuff (FIG. 10). The left-hand end of the strap 170 terminates at the rivet 172, however, the remainder of the strap extends beyond the rivet 173 and continues around the back of the leg to engage the loop 174. After passing through the loop, the elasticized strap portion may be tensioned and secured in place by hook cloth 176 engaging pile cloth 178.

An optional slidably adjustable foam pad 180 may be positioned on the rear of the strap 170. It engages the rear of the leg above the popliteal space 90. It is adjustable lengthwise of the strap 170 by virtue of loops 182 and 184 through which the strap is threaded.

In similar manner, the lower plate 154 is joined to an elasticized strap 190 by a rivet 192. The left-hand portion 191 of the elasticized strap has a loop 193 and is joined to the distal cuff 4 by a rivet 194. The opposite end of the elasticized band 195 is joined by a rivet 198 to the distal cuff 4 and continues around the back of the leg and is engagable wih the loop 196. It, like strap 170, is provided with hook and pile cloth 200 and 202 to adjustably secure it together after passing through the metalic loop 193. A pad 204, similar in shape and function, is adjustably positioned on the strap and engages the rear of the leg below the popliteal space.

The function of super patella plate 152 and the tibia plate 154 will now be described. The super patella plate 152 presses on the large tendion between the femur and the patella. It prevents twisting of the knee and also serves to prevent distal migration, in other words, it stops the brace from sliding downwardly.

The tibia plate 154 floats as the tibia floats, engaging below the patella on the lower patella tendon where it joins the tibia. Jointly, in cooperation with the straps holding the plates tightly to the leg, they prevent rotation of the knee.

The super patella tendion plate 152 and the tibia plate 154 are joined to each other by a pair of crisscross elasticized straps as seen in FIGS. 11 & 12. Strap 210 is secured by a rivet 212 to one proximal edge, i.e., the right-hand side of tibia plate 154 as viewed in FIG. 12. It crosses upwardly and rearwardly and is joined to an adjustable latching means 214 which is secured by a rivet 216 to one distal edge, i.e., the left-hand side of the super patella plate 152. In like manner, an elasticized strap 220 is secured by a rivet 222 to one proximal edge, i.e., the left-hand side of the tibia plate 154 and procedes upwardly and rearwardly and engages with adjustable latching means 226 secured by a rivet 228 to the opposite distal edge, i.e., the right-hand side of the super patella plate. When the brace is placed on the leg, the straps crisscross behind the knee in the popliteal region and are tightened by pulling on the free ends of the straps 210 and 220 through their latching means 214 and 226 respectively. The straps 210 & 220 control the pressure that the super patella plate 152 and its tibia plate apply to the leg.

I claim:

1. A knee orthosis comprising:
    a proximal cuff engageable with a wearer's leg above the knee,
    a distal cuff engageable with the wearer's leg below the knee,
    a pair of polycentric hinges,
    each hinge having a proximal portion pivotally attached to the proximal cuff and a distal portion spaced from the proximal portion and pivotally attached to the distal cuff,
    the proximal portion of both hinges being offset laterally in the same direction relative to the distal portion to prevent pressure to the fibula head,
    the proximal portion of the hinge which is adjacent the outside of the leg being further from the medial of the leg than the distal portion of that hinge and the proximal portion of the hinge which is adjacent the inside of the leg being closer to the medial of the leg than the distal portion of that hinge.

2. A knee orthosis according to claim 1 wherein, the proximal and distal cuffs each have an arcuate portion for engagement with the anterior portion of the wearer's leg above and below the knee respectively, and lateral portions which are pivotally attached to the polycentric hinges.

3. A knee orthosis according to claim 1 wherein, the proximal and distal cuffs and the polycentric hinges are lined with non-allergenic foam padding for direct engagement with the wearer's skin.

4. A knee orthosis according to claim 1 wherein, there are a pair of adjustable, non-elastic straps secured, one each, to the proximal and distal cuffs adjacent to the proximal and distal portions of the polycentric hinges for engagement with the posterior of the wearer's leg above and below above the popliteal space respectively.

5. A knee orthosis according to claim 1 wherein, the cuffs and the polycentric hinges are made of lightweight, high impact thermoplastic which may be shaped to the individual wearer's leg.

6. A knee orthosis according to claim 1 wherein, each polycentric hinge comprises two substantially figure eight shaped members pivotally secured on opposite sides of the proximal and distal cuffs.

7. A knee orthosis according to claim 1 wherein, there are a pair of adjacent elasticized straps secured, one each to the proximal and distal cuffs adjacent to the proximal and distal portions of the polycentric hinges for engagement with the anterior of the wearer's leg above and below the patella.

8. A knee orthosis according to claim 1 wherein there are
    a pair of non-elastic, removable, adjustable straps securable, one each, to the proximal and distal cuffs for engagement with the wearer's posterior thigh and calf respectively to secure the cuffs to the leg.

9. A knee orthosis according to claim 8 wherein, the non-elastic straps have an elastic bridge member on the inner surfaces thereof to permit muscle expansions and contractions of the quadricep and calf.

10. A knee orthosis comprising:
    a proximal cuff engageable with a wearer's leg above the knee,
    a distal cuff engageable with the wearer's leg below the knee,
    a pair of polycentric hinges,
    each hinge having the proximal portion pivotally attached to the proximal cuff and a distal portion spaced from the proximal portion and pivotally attached to the distal cuff,
    the proximal portion of the hinge which is adjacent the outside of the leg being further from the medial of the leg than the distal portion of that hinge and the proximal portion of the hinge which is adjacent the inside of the leg being closer to the medial of the leg than the distal portion of that hinge, the proximal and distal portions of each hinge having stop means to limit the pivotal motion of both the proximal and distal portions of the hinges relative to the proximal and distal cuffs to approximately 180° measured in the anterior direction to prevent the wearer's knee from canting rearwardly.

11. A knee orthosis according to claim 10 wherein, the proximal and distal cuffs each have an arcuate portion for engagement with the anterior portion of the wearer's leg above and below the knee respectively and lateral portions which are pivotally attached to the polycentric hinges.

12. A knee orthosis accroding to claim 10 wherein, the proximal and distal cuffs and the polycentric hinges are lined with non-allergenic foam padding for direct engagement with the wearer's skin.

13. A knee orthosis according to claim 10 wherein, there are a pair of adjustable non-elastic straps secured, one each, to the proximal and distal cuffs adjacent to the proximal and distal portions of the polycentric hinges for engagement with the posterior wearer's leg above and below above the popliteal space respectively.

14. A knee orthosis according to claim 10 wherein, the cuffs and the polycentric hinges are made of lightweight, high impact thermoplastic which may be shaped to the individual wearer's leg.

15. A knee orthosis according to claim 10 wherein, each polycentric hinge comprises two substantially figure eight shaped members pivotally secured on opposite sides of the proximal and distal cuffs.

16. A knee orthosis according to claim 10 wherein, there are a pair of adjacent elasticized straps secured, one each to the proximal and distal cuffs adjacent to the proximal and distal portions of the polycentric hinges for engagement with the anterior of the wearer's leg above and below the patella.

17. A knee orthosis according to claim 10 wherein:
    the stop means to limit the pivotal motion of the hinges comprises a pair of pins fixed in the proximal and distal portions of the polycentric hinges, which pins are engageable by a stop surface formed on each of the proximal and distal cuffs.

18. A knee orthosis according to claim 10 wherein there are
    a pair of non-elastic, removable, adjustable, straps securable, one each, to the proximal and distal cuffs for engagement with the wearer's posterior thigh and calf respectively to secure the cuffs to the leg.

19. A knee orthosis according to claim 18 wherein, the non-elastic straps have an elastic bridge member on the inner surfaces thereof to permit muscle expansions and contractions of the quadricep and calf.

20. A knee orthosis according to claim 18 wherein, the non-elastic straps have an elastic bridge member on the inner surfaces thereof to permit muscle expansions and contractions of the quadricep and calf.

21. A knee orthosis comprising:
a proximal cuff engageable with a wearer's leg above the knee,
a distal cuff engageable with the wearer's leg below the knee,
a pair of polycentric hinges, each hinge having a proximal position pivotally attached to the proximal cuff and a distal portion spaced from the proximal portion and pivotally attached to the distal cuff,
the proximal portion of the hinge which is adjacent the outside of the leg being further from the medial of the leg than the distal portion of that hinge and the proximal portion of the hinge which is adjacent the inside of the leg being closer to the medial of the leg than the distal portion of that hinge, and
an elasticized strap secured to the distal cuff for engagement with the wearer's leg below the knee on the patella tendon.

22. A knee orthosis according to claim 21 wherein, the proximal and distal cuffs each have an arcuate portion for engagement with the anterior portion of the wearer's leg above and below the knee respectively and lateral portions which are pivotally attached to the polycentric hinges.

23. A knee orthosis according to claim 21 wherein, the proximal and distal cuffs and the polycentric hinges are lined with non-allergenic foam padding for direct engagement with the wearer's skin.

24. A knee orthosis according to claim 21 wherein, there is a removable, non-allergenic foam pad secured to the inner surface of the elasticized strap for engagement directly with the wearer's leg on the patella tendon.

25. A knee orthosis according to claim 21 wherein, the cuffs and the polycentric hinges are made of lightweight, high impact thermoplastic which may be shaped to the individual wearer's leg.

26. A knee orthosis according to claim 21 wherein, each polycentric hinge comprises two substantially figure eight shaped members pivotally secured on opposite sides of the proximal and distal cuffs.

27. A knee orthosis according to claim 21 wherein there are
a pair of non-elastic, removable, adjustable straps securable, one each, to the proximal and distal cuffs for engagement with the wearer's posterior thigh and calf respectively to secure the cuffs to the leg.

28. A knee orthosis according to claim 27 wherein, the non-elastic straps have an elastic bridge member on the inner surfaces thereof to permit muscle expansions and contractions of the quadricep and calf.

29. A knee orthosis according to claim 27 wherein, the non-elastic straps have an elastic bridge member on the inner surfaces thereof to permit muscle expansions and contractions of the quadricep and calf.

30. A knee orthosis comprising:
a proximal cuff engageable with a wearer's leg above the knee,
a distal cuff engageable with the wearer's leg below the knee,
a pair of polycentric hinges joining the cuffs,
an anti-rotation structure comprising a patella plate and a tibia plate,
the patella plate and tibia plate being engageable with the leg directly above and directly below the patella respectively,
a pair of adjustable, elasticized straps connecting the patella plate and the tibia plate one strap being secured to a first side of the patella plate and to the opposite side of the tibia plate and the other strap being secured to a second side of the patella plate and to the opposite side of the tibia plate from the first strap, such that they cross one another behind the knee.

31. A knee orthosis according to claim 30 wherein, the plates are lined with non-allergenic foam padding for direct engagement with the wearer's shin.

32. A knee orthosis according to claim 30 wherein, the plates are made of lightweight, high impact, thermoplastic which may be shaped to the individual wearer's leg.

* * * * *